United States Patent [19]

Ofosu-Asanta et al.

[11] Patent Number: 5,474,710

[45] Date of Patent: Dec. 12, 1995

[54] PROCESS FOR PREPARING CONCENTRATED SURFACTANT MIXTURES CONTAINING MAGNESIUM

[76] Inventors: Kofi Ofosu-Asanta; Lawrence C. Grahl, both of The Procter & Gamble Company, Ivorydale Technical Center, Cincinnati, Ohio 45217

[21] Appl. No.: 113,493

[22] Filed: Aug. 27, 1993

[51] Int. Cl.$^6$ .................................................. B01F 17/02
[52] U.S. Cl. ............... 252/352; 252/174.17; 252/174.18; 252/351; 252/353; 252/357
[58] Field of Search ..................... 252/174.17, 174.18, 252/352, 357, 351, 353

[56] References Cited

U.S. PATENT DOCUMENTS

| | | | |
|---|---|---|---|
| 3,719,596 | 3/1973 | Shore et al. | 252/558 X |
| 3,867,301 | 2/1975 | Watanabe et al. | 252/108 |
| 3,872,020 | 3/1975 | Yamagishi et al. | 252/89 |
| 3,910,880 | 10/1975 | Lamberti | 260/210 R |
| 4,364,837 | 12/1982 | Pader | 252/173 |
| 4,488,981 | 12/1984 | Urfer et al. | 252/174.17 |
| 4,536,317 | 8/1985 | Llenado et al. | 252/174.17 |
| 4,536,318 | 8/1985 | Cook et al. | 252/174.17 |
| 4,565,647 | 1/1986 | Llenado | 252/354 |
| 4,599,188 | 7/1986 | Llenado | 252/174.17 |
| 4,663,069 | 5/1987 | Llenado | 252/117 |
| 4,690,818 | 9/1987 | Puchalski, Jr. et al. | 424/70 |
| 4,711,738 | 12/1987 | Copeland | 252/174.17 UX |
| 4,732,696 | 3/1988 | Urfer | 252/174.17 |
| 4,755,318 | 7/1988 | Davies et al. | 252/109 |
| 4,908,159 | 3/1990 | Davies et al. | 252/559 |
| 4,933,101 | 6/1990 | Cilley et al. | 252/174.17 UX |
| 5,015,414 | 5/1991 | Kamegai et al. | 252/174.17 |
| 5,025,069 | 6/1991 | Deguchi et al. | 252/174.17 |
| 5,035,814 | 7/1991 | Maaser | 252/8.7 |
| 5,064,553 | 11/1991 | Dixit et al. | 252/173 X |
| 5,066,425 | 11/1991 | Ofosu-Asante et al. | 252/546 |
| 5,073,293 | 12/1991 | Deguchi et al. | 252/174.17 |
| 5,130,043 | 7/1992 | Prince et al. | 252/174.17 UX |
| 5,154,850 | 10/1992 | Deguchi et al. | 252/174.17 |
| 5,167,872 | 12/1992 | Pancheri et al. | 252/544 |
| 5,188,769 | 2/1993 | Connor et al. | 252/548 |
| 5,229,027 | 7/1993 | Ahmed | 252/173 X |
| 5,232,621 | 8/1993 | Dixit et al. | 252/174.17 UX |
| 5,269,974 | 12/1993 | Ofosu-Asante | 252/174.17 UX |

FOREIGN PATENT DOCUMENTS

| | | | |
|---|---|---|---|
| 0487170 | 5/1992 | European Pat. Off. | C11D 11/00 |
| 0487169 | 5/1992 | European Pat. Off. | C11D 1/655 |
| WO92/06171 | 4/1992 | WIPO . | |
| WO92/08777 | 5/1992 | WIPO . | |
| WO93/03129 | 2/1993 | WIPO | C11D 1/83 |

OTHER PUBLICATIONS

Application Number 07/938,976, inventor Kofi Ofosu–Asante, filing date Sep. 1, 1992.
Application Number 07/938,978, inventor Kofi Ofosu–Asante, filing date Sep. 1, 1992.
Application Number 08/080,736, inventor Kofi Ofosu–Asante, filing date Jun. 22, 1993.
Application Number 08/080,733, inventor Thomas A. Cripe et al., filing date Jun. 22, 1993.

*Primary Examiner*—Paul F. Shaver
*Attorney, Agent, or Firm*—M. P. McMahon

[57] ABSTRACT

A process for preparing a surfactant mixture containing magnesium in which said surfactant mixture is fluidizable. The process comprises neutralizing the surfactant with magnesium hydroxide or magnesium oxide followed by the addition of certain sugars. The resultant surfactant mixture is easily manipulated for use in detergent compositions such as concentrated light duty liquid or gel dishwashing detergent compositions.

11 Claims, No Drawings

PROCESS FOR PREPARING CONCENTRATED SURFACTANT MIXTURES CONTAINING MAGNESIUM

TECHNICAL FIELD

The present invention relates to a process for preparing concentrated surfactant mixtures for use in detergent compositions. The surfactant mixture contains from about 30% to about 70% anionic and/or nonionic surfactant and from about 0.1% to about 5.0% of certain saccharides. The final detergent compositions are preferably light duty liquid or gel dishwashing detergent compositions.

BACKGROUND OF THE INVENTION

Typical light duty liquid or gel dishwashing detergent compositions contain from about 15% to about 30% anionic surfactant. Formulation of concentrated detergent compositions are becoming ever more popular, especially in the laundry and automatic dishwashing detergent compositions. Concentrated compositions address many environmental concerns by reducing the amount of packing and product material needed; however, it is often difficult to formulate stable compositions. This is especially true for detergent compositions containing magnesium (used particularly for its grease cleaning ability in light duty liquid detergent compositions). Concentrated formulation decreases the water content in the product, therefore, the surfactant should be neutralized with magnesium hydroxide or magnesium oxide. This neutralization process, however, results in a a highly viscous middle phase which makes processing impossible.

It has been found that a concentrated magnesium containing surfactant mixture can be formed by mixing certain water-soluble saccharides, i.e sucrose, during the surfactant neutralization step. The concentrated surfactant component is thus easier to handle and to formulate into a detergent composition, particularly a light duty liquid or gel dishwashing detergent composition. Also, the presence of sucrose in such compositions improves the stability and dissolution of the final detergent product.

SUMMARY OF THE INVENTION

The present invention encompasses a process for preparing a concentrated surfactant mixture comprising:

a) forming a neutralization seat comprising from about 0.5% to about 4% magnesium hydroxide or magnesium oxide and from about 0.1% to about 5% sugar; and b) adding to said neutralization seat of step (a) from about 25% to about 50% surfactant acid mix; wherein said surfactant mixture is fluidizable.

A highly preferred process further comprises step c) adding magnesium chloride salt to said mixture of step (b).

The fluidizable surfactant mixture can then be formed into various concentrated detergent products (i.e. light duty liquid or gel dishwashing detergents) in which the saccharide improves product stability and dissolution of the product in wash water.

DETAILED DESCRIPTION OF THE INVENTION

This invention provides a process for preparing a concentrated surfactant mixture. The process comprises:

a) forming a neutralization seat comprising from about 0.5% to about 4% magnesium hydroxide or magnesium oxide and from about 0.1% to about 5% sugar; and b) adding to said neutralization seat of step (a) from about 25% to about 50% surfactant acid mix; wherein said surfactant mixture is fluidizable.

Preferably, the mixture is further processed by adding magnesium chloride salt to said mixture of step (b), and then is used to form a light duty liquid or gel dishwashing detergent composition comprising from about 30% to about 75% by weight anionic surfactant.

Without meaning to be bound by theory, it is believed that the sugar acts as a spacer preventing the surfactant monomers from forming a highly viscous surfactant middle phase which makes the surfactant easier to handle and formulate, i.e. "fluidizable".

The term "light-duty dishwashing detergent composition" as used herein refers to those compositions which are employed in manual (i.e. hand) dishwashing.

By the term "sugar" is meant a mono- or di- saccharide or a derivative thereof, or a degraded starch or chemically modified degraded starch which is water soluble.

The term "neutralization seat" as defined herein means components needed to maintain fluidity while neutralization of surfactants occurs.

Surfactants

The compositions of this invention contain certain surfactants to aid in foaming, detergency, and/or mildness of a final detergent product. The anionic, nonionic and/or amphoteric surfactants are present in a final product in an amount from abut 20% to about 95%, preferably from about 30% to about 75%, more preferably from about 40% to about 70%. The surfactants are present in compositions of the present invention at levels from about 25% to about 50%, preferably 28% to about 45% by weight surfactant.

Included in this category are several anionic surfactants commonly used in liquid or gel dishwashing detergents. The cations associated with these anionic surfactants can be alkali metal, ammonium, mono-, di-, and tri-ethanolammonium, preferably sodium, potassium, ammonium and mixtures thereof. Examples of anionic surfactants that are useful in the present invention are the following classes:

(1) Alkyl benzene sulfonates in which the alkyl group contains from 9 to 15 carbon atoms, preferably 11 to 14 carbon atoms in straight chain or branched chain configuration. An especially preferred linear alkyl benzene sulfonate contains about 12 carbon atoms. U.S. Pat. Nos. 2,220,099 and 2,477,383 describe these surfactants in detail.

(2) Alkyl sulfates obtained by sulfating an alcohol having 8 to 22 carbon atoms, preferably 12 to 16 carbon atoms. The alkyl sulfates have the formula $ROSO_3^-M^+$ where R is the $C_{8-22}$ alkyl group and M is a mono- and/or divalant cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. U.S. Pat. No. 3,332,880 contains a description of suitable olefin sulfonates.

(5) Alkyl ether sulfates derived from ethoxylating an alcohol having 8 to 22 carbon atoms, preferably 12 to 16 carbon atoms, less than 30, preferably less than 12, moles of ethylene oxide. The alkyl ether sulfates having the formula:

$$RO(C_2H_4O)_xSO_3^-M^+$$

where R is the $C_{8-22}$ alkyl group, x is 1–30, and M is a mono- or divalent cation.

(6) Alkyl glyceryl ether sulfonates having 8 to 22 carbon atoms, preferably 12 to 16 carbon atoms, in the alkyl moiety.

(7) Fatty acid ester sulfonates of the formula:

$R_1$—CH($SO_3^-M^+$)$CO_2R_2$ wherein $R_1$ is straight or branched alkyl from about $C_8$ to $C_{18}$, preferably $C_{12}$ to $C_{16}$, and $R_2$ is straight or branched alkyl from about $C_1$ to $C_6$, preferably primarily $C_1$, and $M^+$ represents a mono- or divalent cation.

(8) Secondary alcohol sulfates having 6 to 18 carbon atoms, preferably 8 to 16 carbon atoms.

(9) Alkyl diphenyl oxide disulfonate surfactants of the general formula:

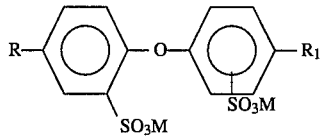

$R=C_{10}-C_{18}$, may be branched or linear
$R_1$=H or R
$M=Na^+, K^+, NH4^+, Ca^{++},$ or $Mg^{++}$

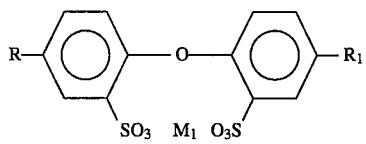

$R=C_{10}-C_{18}$, may be branched or linear
$R_1$=H or R
$M_1=Ca^{++},$ or $Mg^{++}$ Suitable disulfonate surfactants are commercially available under the DOWFAX series from Cow Chemical (Dowfax 2A1, 3B2, 8290) and the POLY-TERGENT series from Olin Corp.

(10) The following general structures illustrate some of the special soaps (or their precursor acids) employed in this invention.

A. A highly preferred class of soaps used herein comprises the $C_{10}-C_{16}$ secondary carboxyl materials of the formula $R^3$ CH($R^4$)COOM, wherein $R^3$ is $CH_3(CH_2)_x$ and $R^4$ is $CH_3(CH_2)_y$, wherein y can be 0 or an integer from 1 to 6, x is an integer from 6 to 12 and the sum of (x+y) is 6–12, preferably 7–11, most preferably 8–9.

B. Another class of special soaps useful herein comprises those carboxyl compounds wherein the carboxyl substituent is on a ring hydrocarbyl unit, i.e., secondary soaps of the formula $R^5$—$R^6$—COOM, wherein $R^5$ is $C_7-C_{10}$, preferably $C_8-C_9$, alkyl or alkenyl and $R^6$ is a ring structure, such as benzene, cyclopentane, cyclohexane, and the like. (Note: $R^5$ can be in the ortho, meta or para position relative to the carboxyl on the ring.)

C. Still another class of soaps includes the $C_{10}-C_{18}$ primary and secondary carboxyl compounds of the formula $R^7$CH($R^8$)COOM, wherein the sum of the carbons in $R^7$ and $R^8$ is 8–16, $R^7$ is of the form $CH_3$—($CHR^9$)$_x$ and $R^8$ is of the form H—($CHR^9$)$_y$, where x and y are integers in the range 0–15 and $R^9$ is H or a $C_{1-4}$ linear or branched alkyl group. $R^9$ can be any combination of H and $C_{1-4}$ linear or branched alkyl group members within a single —($CHR^9$)$_{x,y}$ group; however, each molecule in this class must contain at least one $R^9$ that is not H. These types of molecules can be made by numerous methods, e.g. by hydroformylation and oxidation of branched olefins, hydroxycarboxylation of branched olefins, oxidation of the products of Guerbet reaction involving branched oxoalcohols. The branched olefins can be derived by oligomerization of shorter olefins, e.g. butene, isobutylene, branched hexene, propylene and pentene.

D. Yet another class of soaps includes the $C_{10}-C_{18}$ tertiary carboxyl compounds, e.g., neo-acids, of the formula $R^{10}CR^{11}(R^{12})COOM$, wherein the sum of the carbons in $R^{10}$, $R^{11}$ and $R^{12}$ is 8–16. $R^{10}$, $R^{11}$, $R^{12}$ are of the form $CH_3$—($CHR^{13}$)$_x$, where x is an integer in the range 0–13, and $R^{13}$ is H or a $C_{1-4}$ linear or branched alkyl group. Note that $R^{13}$ can be any combination of H and $C_{1-4}$ linear or branched alkyl group members within a single —($CHR^{13}$)$_x$ group. These types of molecules result from addition of a carboxyl group to a branched olefin, e.g., by the Koch reaction. Commercial examples include the neodecanoic acid manufactured by Exxon, and the Versatic™ acids manufactured by Shell.

In each of the above formulas A, B, C and D, the species M can be any suitable, especially water-solubilizing, counterion, e.g., H, alkali metal, alkaline earth metal, ammonium, alkanolammonium, di- and tri- alkanolammonium, $C_1-C_5$ alkyl substituted ammonium and the like. Sodium is convenient, as is diethanolammonium.

Preferred secondary soaps for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid; 2-pentyl-1-heptanoic acid; 2-methyl-1-dodecanoic acid; 2-ethyl-1-undecanoic acid; 2-propyl-1-decanoic acid; 2-butyl-1-nonanoic acid; 2-pentyl-1-octanoic acid and mixtures thereof

(11) Mixtures thereof.

The above described anionic surfactants are all available commercially. It should be noted that although both dialkyl sulfosuccinates and fatty acid ester sulfonates will function well at neutral to slightly alkaline pH, they will not be chemically stable in a composition with pH much greater than about 8.5.

Other useful surfactants for use in the compositions are the nonionic fatty alkylpolyglucosides. These surfactants contain straight chain or branched chain $C_8$ to $C_{15}$, preferably from about $C_{12}$ to $C_{14}$, alkyl groups and have an average of from about 1 to 5 glucose units, with an average of 1 to 2 glucose units being most preferred. U.S. Pat. Nos. 4,393,203 and 4,732,704, incorporated by reference, describe these surfactants.

The compositions hereof may also contain a polyhydroxy fatty acid amide surfactant of the structural formula:

(I)

wherein: $R^1$ is H, $C_1-C_4$ hydrocarbyl, 2-hydroxy ethyl, 2-hydroxy propyl, or a mixture thereof, preferably $C_1-C_4$ alkyl, more preferably $C_1$ or $C_2$ alkyl, most preferably $C_1$ alkyl (i.e., methyl); and $R^2$ is a $C_5-C_{31}$ hydrocarbyl, preferably straight chain $C_7-C_{19}$ alkyl or alkenyl, more preferably straight chain $C_9-C_{17}$ alkyl or alkenyl, most preferably straight chain $C_{11}-C_{17}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly —$CH_2$—$(CHOH)_4$—$CH_2OH$.

In Formula (I), $R^1$ can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Methods for making polyhydroxy fatty acid amides are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensation/amidation step to form the N-alkyl, N-polyhydroxy fatty acid amide product. Processes for making compositions containing polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

In a preferred process for producing N-alkyl or N-hydroxyalkyl, N-deoxyglycityl fatty acid amides wherein the glycityl component is derived from glucose and the N-alkyl or N-hydroxyalkyl functionality is N-methyl, N-ethyl, N-propyl, N-butyl, N-hydroxyethyl, or N-hydroxy-propyl, the product is made by reacting N-alkyl- or N-hydroxyalkyl-glucamine with a fatty ester selected from fatty methyl esters, fatty ethyl esters, and fatty triglycerides in the presence of a catalyst selected from the group consisting of trilithium phosphate, trisodium phosphate, tripotassium phosphate, tetrasodium pyrophosphate, pentapotassium tripolyphosphate, lithium hydroxide, sodium hydroxide, potassium hydroxide, calcium hydroxide, lithium carbonate, sodium carbonate, potassium carbonate, disodium tartrate, dipotassium tartrate, sodium potassium tartrate, trisodium citrate, tripotassium citrate, sodium basic silicates, potassium basic silicates, sodium basic aluminosilicates, and potassium basic aluminosilicates, and mixtures thereof. The amount of catalyst is preferably from about 0.5 mole % to about 50 mole %, more preferably from about 2.0 mole % to about 10 mole %, on an N-alkyl or N-hydroxyalkyl-glucamine molar basis. The reaction is preferably carried out at from about 138° C. to about 170° C. for typically from about 20 to about 90 minutes. When triglycerides are utilized in the reaction mixture as the fatty ester source, the reaction is also preferably carried out using from about 1 to about 10 weight % of a phase transfer agent, calculated on a weight percent basis of total reaction mixture, selected from saturated fatty alcohol polyethoxylates, alkylpolyglycosides, linear glycamide surfactant, and mixtures thereof.

Preferably, this process is carried out as follows:

(a) preheating the fatty ester to about 138° C. to about 170°C.;

(b) adding the N-alkyl or N-hydroxyalkyl glucamine to the heated fatty acid ester and mixing to the extent needed to form a two-phase liquid/liquid mixture;

(c) mixing the catalyst into the reaction mixture; and (d) stirring for the specified reaction time.

Also preferably, from about 2% to about 20% of preformed linear N-alkyl/N-hydroxyalkyl, N-linear glucosyl fatty acid amide product is added to the reaction mixture, by weight of the reactants, as the phase transfer agent if the fatty ester is a triglyceride. This seeds the reaction, thereby increasing reaction rate.

These polyhydroxy "fatty acid" amide materials also offer the advantages to the detergent formulator that they can be prepared wholly or primarily from natural, renewable, non-petrochemical feedstocks and are degradable. They also exhibit low toxicity to aquatic life.

It should be recognized that along with the polyhydroxy fatty acid amides of Formula (I), the processes used to produce them will also typically produce quantities of nonvolatile by-product such as esteramides and cyclic polyhydroxy fatty acid amide. The level of these by-products will vary depending upon the particular reactants and process conditions. Preferably, the polyhydroxy fatty acid amide incorporated into the detergent compositions hereof will be provided in a form such that the polyhydroxy fatty acid amide-containing composition added to the detergent contains less than about 10%, preferably less than about 4%, of cyclic polyhydroxy fatty acid amide. The preferred processes described above are advantageous in that they can yield rather low levels of by-products, including such cyclic amide by-product.

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from 6 to 12 carbon atoms in either a straight- or branched-chain configuration with the alkylene oxide. Commercially available nonionic surfactants of this type include Igepal™ CO-630, marketed by the GAF Corporation; and Triton™ X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from about 10 to about 20 carbon atoms with from about 2 to about 10 moles of ethylene oxide per mole of alcohol.

3. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility.

4. The condensation products of ethylene oxide with the product resulting from the reaction of propylene oxide and ethylenediamine.

5. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. U.S. Pat. Nos. 4,373,203 and 4,732,704, incorporated herein by reference, also describe acceptable surfactants.

6. Alkyl ethoxy carboxylates of the generic formula $RO(CH_2CH_2O)_xCH_2COO^-M^+$ wherein R is a $C_{12}$ to $C_{16}$ alkyl group, x ranges from 0 to about 10, and the ethoxylate distribution is such that, on a weight basis, the amount of material where x is 0 is less than about 20%, preferably less than about 15%, most preferably less than about 10%, and the amount of material where x is greater than 7 is less than about 25%, preferably less than about 15%, most preferably less than about 10%, the average x is from about 2 to 4 when the average R is $C_{13}$ or less, and the average x is from about 3 to 6 when the average R is greater than $C_{13}$, and M is a cation preferably chosen from alkali metal, ammonium, mono-, di-, and tri-ethanolammonium, most preferably from sodium, potassium, ammonium, and mixtures thereof. The preferred alkyl ethoxy carboxylates are those where R is a $C_{12}$ to $C_{14}$ alkyl group. Suitable processes for producing the alkyl ethoxy carboxylates are disclosed in U.S. Pat. No. 5,233,087, incorporated herein by reference.

Other suitable surfactants such as ampholytic surfactants may also be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight-branched chains. One of the aliphatic substituents contains at least 8 carbon atoms, typically from 8 to 18 carbon atoms, and at least one contains an anionic water-solubilizing group, e.g., carboxy, sulfonate, sulfate. See U.S. Pat. No. 3,929,678 to Laughlin et al., issued Dec. 30, 1975, at column 19, lines 18–35 (herein incorporated by reference) for examples of useful ampholytic surfactants.

Alkyl amphocarboxylic acids can be added of the generic formula

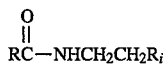

wherein R is a $C_8$–$C_{18}$ alkyl group, and $R_i$ is of the general formula

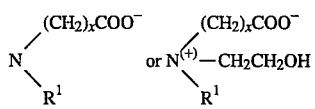

wherein $R^1$ is a $(CH_2)_xCOOM$ or $CH_2CH_2OH$, and x is 1 or 2 and M is preferably chosen from alkali metal, alkaline earth metal, ammonium, mono-, di-, and tri-ethanolammonium, most preferably from sodium, potassium, ammonium, and mixtures thereof with magnesium ions. The preferred R alkyl chain length is a $C_{10}$ to $C_{14}$ alkyl group.

In a preferred embodiment, the amphocarboxylic acid is an amphodicarboxylic acid produced from fatty imidazolines wherein the dicarboxylic acid functionality of the amphodicarboxylic acid is diacetic acid and/or dipropionic acid. A suitable example of an alkyl amphodicarboxylic acid for use herein is the amphoteric surfactant Miranol® C2M Conc. manufactured by Miranol, Inc., Dayton, N.J., having the general formula

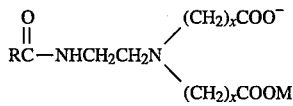

wherein R is a $C_8$ to $C_{18}$ alkyl group, and x is 1 or 2, and M is a cation.

Zwitterionic surfactants may also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975, at column 19, line 38 through column 22, line 48 (herein incorporated by reference) for examples of useful zwitterionic surfactants.

Such ampholytic and zwitterionic surfactants are generally used in combination with one or more anionic and/or nonionic surfactants.

If included in the compositions of the present invention, these additional surfactants are typically present at a concentration of from about 1% to about 15%, preferably from about 2% to about 10% by weight of the composition.

Magnesium Ions

The presence of magnesium (divalent) ions, improves the cleaning of greasy soils of light duty liquid or gel compositions. This is especially true when the compositions are used in softened water that contains few divalent ions. The amount of magnesium ions present in such compositions hereof are at a level of from about 0.1% to 4%, preferably from about 0.3% to 3.5%, more preferably from about 0.5% to 1%, by weight.

In formulating concentrated compositions containing magnesium ions, especially light duty liquid or gel dishwashing detergent compositions, neutralizing the surfactant with magnesium hydroxide or magnesium oxide is necessary. This provides a source for magnesium ions and decreases the amount of water added to the final composition. The amount of magnesium hydroxide and/or oxide used in the neutralization step comprises from about 0.5% to about 5%, preferably from about 0.5% to about 3%, by weight of the surfactant mixture.

Additional magnesium ions may be added to the final product as chloride, acetate, formate, nitrate salt or mixtures thereof.

The amount of magnesium included in the final detergent products will be dependent upon the amount of total anionic surfactant present therein, including the amount of alkyl ethoxy carboxylates. When calcium ions are present in the compositions of this invention, the molar ratio of magnesium ions to total anionic surfactant is from about 1:15 to about 1:2 for compositions of the invention.

Saccharides

The present invention comprises from about 0.1% to about 5.0%, preferably from about 0.5% to about 4.0% of a mono- or di- saccharide. The saccharide repeating unit can have as few as five carbon atoms or as many as fifty carbon atoms consistent with water solubility. The saccharide derivative can be an alcohol or acid of the saccharide. By "water-soluble" in the present context it is meant that the sugar is capable of forming a clear solution or a stable colloidal dispersion in distilled water at room temperature at a concentration of 0.01 g/l.

Amongst the sugars which are useful in this invention are sucrose, which is most preferred for reasons of availability and cheapness, maltose (malt sugar), cellobiose, lactulose and lactose which are disaccharides. Useful mon-saccharide derivatives include gluconic acid, glucose, fructose, galactose, xylose, ribose and mixtures thereof.

For ease of formulation the sugar is added as a solution, said solution comprising from about 0.15% to about 70%, preferably from about 0.5% to about 65% sugar in water.

Suds Booster

Another component which may be included in the composition of this invention is a suds stabilizing surfactant (suds booster) at a level of less than about 15%, preferably from about 0.5% to 12%, more preferably from about 1% to 10%. Optional suds stabilizing surfactants operable in the instant composition are: betaines, sultaines, complex betaines, ethylene oxide condensates, fatty acid amides, amine oxide semi-polar nonionics, and cationic surfactants. These components may be added in a neutralization paste and/or at a later step of the final product formulation.

ably, hydroxyalkylene group. Examples of suitable sultaines include $C_{12}$–$C_{14}$ dimethylammonio-2-hydroxypropyl sulfonate, $C_{12-14}$ amido propyl ammonio-2-hydroxypropyl sultaine, $C_{12-14}$ dihydroxyethylammonio propane sulfonate, and $C_{16-18}$ dimethylammonio hexane sulfonate, with $C_{12-14}$ amido propyl ammonio-2-hydroxypropyl sultaine being preferred.

The complex betaines for use herein have the formula

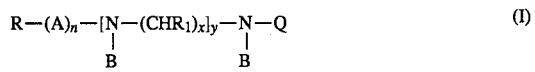

wherein R is a hydrocarbon group having from 7 to 22 carbon atoms, A is the group (C(O), n is 0 or 1, $R_1$ is hydrogen or a lower alkyl group, x is 2 or 3, y is an integer of 0 to 4, Q is the group —$R_2$COOM wherein $R_2$ is an alkylene group having from 1 to 6 carbon atoms and M is hydrogen or an ion from the groups alkali metals, alkaline earth metals, ammonium and substituted ammonium and B is hydrogen or a group Q as defined.

An example in this category is alkylamphopolycarboxy glycinate, of the formula:

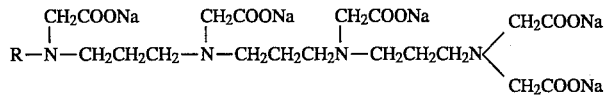

The composition of this invention can contain betaine detergent surfactants having the general formula:

R—N(+)($R^1$)$_2$—$R^2$COO(-)

wherein R is a hydrophobic group selected from the group consisting of alkyl groups containing from about 10 to about 22 carbon atoms, preferably from about 12 to about 18 carbon atoms, alkyl aryl and aryl alkyl groups containing a similar number of carbon atoms with a benzene ring being treated as equivalent to about 2 carbon atoms, and similar structures interrupted by amido or ether linkages; each $R^1$ is an alkyl group containing from 1 to about 3 carbon atoms; and $R^2$ is an alkylene group containing from 1 to about 6 carbon atoms.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate.

Other suitable amidoalkylbetaines are disclosed in U.S. Pat. Nos. 3,950,417; 4,137,191; and 4,375,421; and British Patent GB No. 2,103,236, all of which are incorporated herein by reference.

It will be recognized that the alkyl (and acyl) groups for the above betaine surfactants can be derived from either natural or synthetic sources, e.g., they can be derived from naturally occurring fatty acids; olefins such as those prepared by Ziegler, or Oxo processes; or from olefins separated from petroleum either with or without "cracking".

The sultaines useful in the present invention are those compounds having the formula (R($R^1$)$_2$$N^+$$R^2$$SO_3$— wherein R is a $C_6$–$C_{18}$ hydrocarbyl group, preferably a $C_{10}$–$C_{16}$ alkyl group, more preferably a $C_{12}$–$C_{13}$ alkyl group, each $R^1$ is typically $C_1$–$C_3$ alkyl, preferably methyl, and $R^2$ is a $C_1$–$C_6$ hydrocarbyl group, preferably a $C_1$–$C_3$ alkylene or, prefer- The ethylene oxide condensates are broadly defined as compounds produced by the condensation of ethylene oxide groups (hydrophilic in nature) with an organic hydrophobic compound, which can be aliphatic or alkyl aromatic in nature. The length of the hydrophilic or polyoxyalkylene radical which is condensed with any particular hydrophobic group can be readily adjusted to yield a water-soluble compound having the desired balance between hydrophilic and hydrophobic elements.

Examples of such ethylene oxide condensates suitable as suds stabilizers are the condensation products of aliphatic alcohols with ethylene oxide. The alkyl chain of the aliphatic alcohol can either be straight or branched and generally contains from about 8 to about 18, preferably from about 8 to about 14, carbon atoms for best performance as suds stabilizers, the ethylene oxide being present in amounts of from about 8 moles to about 30, preferably from about 8 to about 14 moles of ethylene oxide per mole of alcohol.

Examples of the amide surfactants useful herein include the ammonia, monoethanol, and diethanol amides of fatty acids having an acyl moiety containing from about 8 to about 18 carbon atoms and represented by the general formula:

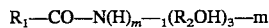

wherein R is a saturated or unsaturated, aliphatic hydrocarbon radical having from about 7 to 21, preferably from about 11 to 17 carbon atoms; $R_2$ represents a methylene or ethylene group; and m is 1, 2, or 3, preferably 1. Specific examples of said amides are mono-ethanol amine coconut fatty acid amide and diethanol amine dodecyl fatty acid amide. These acyl moieties may be derived from naturally occurring glycerides, e.g., coconut oil, palm oil, soybean oil, and tallow, but can be derived synthetically, e.g., by the oxidation of petroleum or by hydrogenation of carbon monoxide by the Fischer-Tropsch process. The monoethanol amides and diethanolamides of $C_{12-14}$ fatty acids are preferred.

Amine oxide semi-polar nonionic surfactants comprise compounds and mixtures of compounds having the formula

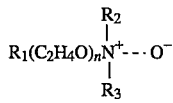

wherein $R_1$ is an alkyl, 2-hydroxyalkyl, 3-hydroxyalkyl, or 3-alkoxy-2-hydroxypropyl radical in which the alkyl and alkoxy, respectively, contain from about 8 to about 18 carbon atoms, $R_2$ and $R_3$ are each methyl, ethyl, propyl, isopropyl, 2-hydroxyethyl, 2-hydroxypropyl, or 3-hydroxypropyl, and n is from 0 to about 10. Particularly preferred are amine oxides of the formula:

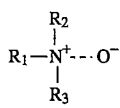

wherein $R_1$ is a $C_{12-16}$ alkyl and $R_2$ and $R_3$ are methyl or ethyl. The above ethylene oxide condensates, amides, and amine oxides are more fully described in U.S. Pat. No. 4,316,824 (Pancheri), incorporated herein by reference.

The composition of this invention can also contain certain cationic quarternary ammonium surfactants of the formula:

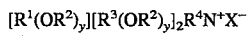

or amine surfactants of the formula:

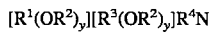

wherein $R^1$ is an alkyl or alkyl benzyl group having from about 6 to about 16 carbon atoms in the alkyl chain; each $R^2$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^3$ is selected from the group consisting of $C_1$–$C_4$ alkyl, $C_1$–$C_4$ hydroxyalkyl, benzyl, and hydrogen when y is not 0; $R^4$ is the same as $R^3$ or is an alkyl chain wherein the total number of carbon atoms of $R^1$ plus $R^4$ is from about 8 to about 16; each y is from 0 to about 10, and the sum of the y values is from 0 to about 15; and X is any compatible anion.

Preferred of the above are the alkyl quaternary ammonium surfactants, especially the mono-long chain alkyl surfactants described in the above formula when $R^4$ is selected from the same groups as $R^3$. The most preferred quaternary ammonium surfactants are the chloride, bromide, and methylsulfate $C_{8-16}$ alkyl trimethylammonium salts, $C_{8-16}$ alkyl di(hydroxyethyl)methylammonium salts, the $C_{8-16}$ alkyl hydroxyethyldimethylammonium salts, $C_{8-16}$ alkyloxypropyl trimethylammonium salts, and the $C_{8-16}$ alkyloxypropyl dihydroxyethylmethylammonium salts. Of the above, the $C_{10-14}$ alkyl trimethylammonium salts are preferred, e.g., decyl trimethylammonium methylsulfate, lauryl trimethylammonium chloride, myristyl trimethylammonium bromide and coconut trimethylammonium chloride, and methylsulfate.

The suds boosters used in the compositions of this invention can contain any one or mixture of the suds boosters listed above.

pH of the Composition

Preferably the final light duty liquid or gel dishwashing detergent composition of the present invention has a pH in a 10% solution in water at 20° C. between about 7 and about 11, more preferably between about 7.5 and about 10, most preferably from about 7.5 to about 8.3.

Dishwashing compositions of the invention will be subjected to acidic stresses created by food soils when put to use, i.e., diluted and applied to soiled dishes. If a composition with a pH greater than 7 is to be more effective in improving performance, it should contain a buffering agent capable of maintaining the alkaline pH in the composition and in dilute solutions, i.e., about 0.1% to 0.4% by weight aqueous solution, of the composition. The pKa value of this buffering agent should be about 0.5 to 1.0 pH units below the desired pH value of the composition (determined as described above). Preferably, the pKa of the buffering agent should be from about 7 to about 9.5. Under these conditions the buffering agent most effectively controls the pH while using the least amount thereof.

The buffering agent may be an active detergent in its own right, or it may be a low molecular weight, organic or inorganic material that is used in this composition solely for maintaining an alkaline pH. Preferred buffering agents for compositions of this invention are nitrogen-containing materials. Some examples are amino acids or lower alcohol amines like mono-, di-, and tri-ethanolamine. Other preferred nitrogen-containing buffering agents are 2-amino-2-ethyl-1,3-propanediol, 2-amino-2-methylpropanol, 2-amino-2-methyl-1,3-propanediol, tris-(hydroxymethyl)aminomethane (a.k.a. tris) and disodium glutamate. N-methyl diethanolamine, 1,3-diamino-2-propanol N,N'-tetramethyl-1,3-diamino-2-propanol, N,N-bis(2-hydroxyethyl)glycine (a.k.a. bicine), and N-tris (hydroxymethyl)methyl glycine (a.k.a. tricine) are also preferred. Mixtures of any of the above are acceptable.

The buffering agent is present in the compositions of the invention hereof at a level of from about 0.1% to 15%, preferably from about 1% to 10%, most preferably from about 2% to 8%, by weight of the composition.

Additional Optional Ingredients

In addition to the ingredients described hereinbefore, the compositions can further contain other conventional ingredients suitable for use in detergent compositions, preferably light duty liquid or gel dishwashing detergent compositions. These ingredients may be added in the neutralization paste and/or after formulation of the fluidized surfactant mixture.

Preferably, the magnesium or calcium ions are added as a chloride, acetate, formate or nitrate salt to compositions containing an alkali metal or ammonium salt of the alkyl ethoxy carboxylate, most preferably the sodium salt, after the composition has been neutralized with a strong base.

Optional ingredients include drainage promoting ethoxylated nonionic surfactants of the type disclosed in U.S. Pat. No. 4,316,824, Pancheri (Feb. 23, 1982), incorporated herein by reference.

Alcohols, such as $C_1$–$C_4$ monohydric alcohols, and additional hydrotropes, such as calcium, sodium or potassium toluene, xylene or cumene sulfonate, can be utilized in addition to water in the interests of achieving a desired product phase stability and viscosity. Preferably a mixture of water and a $C_1$–$C_4$ monohydric alcohol (e.g., ethanol, propanol, isopropanol, butanol, and mixtures thereof), with ethanol being the preferred alcohol. Alcohols and/or hydrotropes are present at a level of from 0% to about 15%, preferably from about 0.1% 5 to 10%. The viscosity should be greater than about 100 centipoise, more preferably more than 150 centipoise, most preferably more than about 200 centipoise for consumer acceptance.

Gel compositions of the invention normally would not contain alcohols. These gel compositions may contain levels of urea and conventional thickeners at levels from about 10% to about 30%, as gelling agents.

Other desirable ingredients include diluents and solvents. Diluents can be inorganic salts, such as ammonium chloride, sodium chloride, potassium chloride, etc., and the solvents include water, lower molecular weight alcohols, such as ethyl alcohol, isopropyl alcohol, etc. Compositions herein will typically contain up to about 80%, preferably from about 30% to about 70%, most preferably from about 40% to about 65%, of water.

The Process

Generally, various processes can be used to form the surfactant mixtures of the present invention. One preferred method comprises:

a) mixing about 10% water, about 5.6% of a 40% active sodium xylene sulfonate, about 9% ethanol, about 1.5% saccharide and about 2.2% magnesium hydroxide;

b) adding to the mixture of step (a) about 6.9% of a 29% active cooamidopropyl betaine solution and about 8.6% of a 35% active akyl amine oxide solution;

c) adding with vigorous stirring to the mixture of step (b) about 12.3% of a 53% active polyhydroxy fatty acid amide (containing about 5% propylene glycol or 5% magnesium chloride), said polyhydroxy fatty acid amide having been heated at about 90° F. to about 100° F.;

d) stirring into the mixture (a.k.a. neutralization seat) of step (c) the alkyl sulfuric acid and alkyl ether sulfuric acid; wherein said stirring of step (c) is throrough, i.e. the magnesium appears completely dissolved;

e) adjusting the pH up to between about 6 and about 7.

The polyhydroxy fatty acid amide of step (c) can be made using the following process:

(a) preheating the fatty ester and solvent to about 60° C.–70° C.;

(b) adding the N-alkyl glucamine to the heated fatty ester of step (a) and setting the pressure to 100 mm Hg;

(c) heating to 80° C. and removing water and solvent by vacuum;

(d) adding water and warming to from about 40° C. to about 50° C.;

(e) adding base catalyst and reacting without reflux;

(f) agitating and mixing at from about 60° C. to about 70° C.;

(g) adjusting the pH;

(h) adding and mixing from about 0.1% to about 10% of any soluble salt which is not a sodium and/or ammonium salt or propyl glycol; and (i) stirring until the salt is dissolved.

When the salt is a magnesium salt, the pH at step (g) should be adjusted to a pH of from about 7 to about 7.5. Other metal salts can be added in a more alkaline environment (e.g. pH about 7.5 to 9.0). The polyhydroxy fatty acid amide composition herein preferably has a pH between about 7.0 and about 9.0.

An alternative process for forming polyhydroxy fatty acid amide is as follows.

(a) heating at least about 90%, by weight of the polyhydroxy fatty acid amide composition, of a solid polyhydroxy fatty acid amide mixture consisting of from about 40% to about 95% of polyhydroxy fatty acid amide, to from about 60° C. to about 80° C.;

(b) adding and stirring in from about 0.01% to about 10%, by weight of the polyhydroxy fatty acid composition, of a salt as described above; and (c) stirring until the salt is dissolved.

The polyhydroxy fatty acid amide composition herein is made pumpable, which means it can easily be transferred from place to place in the plant. It can now be metered more easily and it is more easily combined with other ingredients in a composition, preferably a liquid detergent composition, more preferably a stable light duty liquid comprising from about 0.005% to about 95% by weight of anionic and/or nonionic surfactant, and from about 5% to about 50% by weight of polyhydroxy fatty acid amide composition as described above. Liquid detergent compositions herein preferably have a pH between about 7.0 and about 9.0. The polyhydroxy fatty acid amide composition (i.e. salt already added) remains in a liquid state, usually clear, at temperatures below the normal melting point ranges for polyhydroxy fatty acid amide (e.g. polyhydroxy fatty acid amide compositions can remain in a liquid state for about three weeks at 80° to 100° F., which is 40° to 60° F. below that of a 50% n-cocacyl N-methyl polyhydroxy fatty acid amide mixture). The same amounts and ingredients described above also are preferred in the polyhydroxy fatty acid amide composition. Preferably, the detergent composition comprises from about 5% to about 40%, more preferably from about 5% to about 30%, most preferably from about 8% to about 25%, by weight, of the polyhydroxy fatty acid amide composition described above.

The polyhydroxy fatty acid amide composition can be added to the neutralization seat.

As used herein, all percentages, parts, and ratios are by weight unless otherwise stated.

The following Examples illustrate the invention and facilitate its understanding.

EXAMPLE I

Detergent pastes (neutralization seat pastes) are prepared by making a slurry of water, ethanol, amine oxide, cocoamidopropyl betaine, magnesium hydroxide with or without the saccharide and/or magnesium chloride. The alkyl ethoxy sulfuric acid (surfactant acid mix) is then added to the slurry (paste).

| Ingredients | Composition % by weight | | |
| --- | --- | --- | --- |
| | A | B | C |
| Ethanol | 9 | 9 | 7 |
| Alkyl amine oxide | 2 | 2 | 2 |
| Cocoamidopropyl betaine | 3 | 3 | 3 |
| Magnesium hydroxide | 2 | 2 | 1.5 |
| Magnesium chloride hexahydrate | 0 | 0 | 1.7 |
| Sucrose | 0 | 1.5 | 1.5 |
| Alkyl ethoxy sulfuric acid ethoxy (avg. 0–1) | 37 | 37 | 37 |
| Water | | balance | |
| pH | 2 | 2 | 2 |

Compositions B and C containing sucrose are readily mixable, whereas Composition A is not.

EXAMPLE II

The following light duty liquid detergent compositions are prepared according to the descriptions set forth above.

The surfactant is neutralized in a paste and the saccharide is blended. The other ingredients are then added to form the final detergent product.

| Components | % by Weight | |
| --- | --- | --- |
| | D | E |
| Diethylene penta acetate | 0.06 | 0.06 |
| Ethanol | 9.15 | 9.15 |
| Magnesium hydroxide | 2.18 | 2.18 |
| Sucrose | 1.50 | 1.50 |
| Alkyl ethoxy sulfate | 34.14 | 34.14 |
| Sodium hydroxide | 1.13 | 1.13 |
| Polyhydroxy fatty acid amide | 6.50 | 6.50 |
| Amine oxide | 3.00 | 3.00 |
| Cocoamidopropyl Betaine | 2.00 | 2.00 |
| Perfume | 0.23 | 0.23 |
| Calcium xylene sulfonate | 3.59 | 2.05 |
| Calcium chloride | 0.00 | 0.53 |
| Water | balance | |

EXAMPLE III

The following light duty liquid compositions of the present invention are prepared as set forth above wherein the surfactant is acid neutralized with magnesium hydroxide.

| Component | % by weight | |
| --- | --- | --- |
| | F | G |
| Citric acid | 0.05 | 0.00 |
| Sodium toluene sulfonate | 3.00 | 0.00 |
| Ethanol | 5.50 | 0.00 |
| Sodium C12–13 alkyl ethoxy (1.0 ave.) sulfate | 31.00 | 24.00 |
| Sodium C12–13 alkyl ethoxy (3.0 ave.) sulfate | 8.00 | 7.00 |
| Amine oxide | 2.00 | 2.00 |
| C12 alkyl N-methyl glucamide and magnesium chloride | 9.00 | 12.00 |
| Magnesium chloride hexahydrate | 0.90 | 1.84 |
| Perfume | 0.90 | 0.18 |
| Sucrose | 2.00 | 1.00 |
| Calcium chloride | 0.00 | 0.15 |
| Sodium cumene sulfonate | 0.00 | 4.0 |
| $C_{9-11}$ alcohol-polyethoxylate (9.0) | 0.00 | 5.0 |
| Water, trim | Balance | |
| pH = 7.1 at 10% | | |

What is claimed is:

1. A process for preparing a concentrated surfactant mixture, which process comprises the steps of:

a) forming a neutralization seat comprising from about 0.5% to about 4% magnesium hydroxide or magnesium oxide and from about 0.1% to about 5% sugar; and b) adding to said neutralization seat of step (a) from about 25% to about 45% of a surfactant acid mix; to thereby form a concentrated surfactant mixture which is fluidizable.

2. A process according to claim 1 wherein said sugar is selected from the group consisting of monosaccharides and disaccharides.

3. A process according to claim 2 further comprising step (c) adding magnesium chloride salt to said mixture of step (b).

4. A process according to claim 1 wherein during step (b) said neutralization seat is maintained under agitation by stirring.

5. A process according to claim 2 wherein said surfactant is selected from the group consisting of anionic surfactants, nonionic surfactants, amphoteric surfactants and mixtures thereof.

6. A process according to claim 5 wherein the neutralization seat formed in step (a) further comprises from about 0.5% to about 12% suds booster.

7. A process according to claim 5 comprising from about 0.5% to about 4% of sugar.

8. A process according to claim 7 wherein said sugar is selected from the group consisting of sucrose, maltose, celloboise, lactose, gluconic acid, glucose, fructose, galactose, xylose, ribose and mixtures thereof.

9. A process for preparing a concentrated surfactant mixture, which process comprises the steps of:

a) forming a neutralization scat consisting essentially of magnesium hydroxide, sodium xylene sulfonate, suds booster selected from the group consisting of betaines and semi-polar amine oxides, polyhydroxy fatty acid amide, magnesium chloride, propylene glycol, and sucrose;

b) adding to said neutralization seat of step (a) from about 25% to about 45% of a surfactant acid selected from the group consisting of alkyl sulfuric acid and alkyl ether sulfuric acid;

to thereby form a concentrated surfactant mixture which is fluidizable and which has a pH between about 6 and about 7, after treatment with organic or inorganic base.

10. A process according to claim 6 wherein the pH of said concentrated surfactant mixture is between pH about 6 and about 7.

11. A process according to claim 9 wherein said polyhydroxy fatty acid amide of step (a) is melted at about 90° F. to about 100° F.

* * * * *